(12) United States Patent
Vigneaux et al.

(10) Patent No.: US 6,508,105 B1
(45) Date of Patent: Jan. 21, 2003

(54) APPARATUS AND METHOD FOR MEASURING THE CHARACTERISTICS OF AN OILFIELD FLUID OR THE LIKE

(75) Inventors: Pierre Vigneaux, Moisenay (FR); Dominique Guillot, Fontenay aux roses (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 09/831,528

(22) PCT Filed: Nov. 5, 1999

(86) PCT No.: PCT/EP99/08696

§ 371 (c)(1),
(2), (4) Date: Jul. 27, 2001

(87) PCT Pub. No.: WO00/29845

PCT Pub. Date: May 25, 2000

(30) Foreign Application Priority Data

Nov. 12, 1998 (FR) .............................. 98 14223

(51) Int. Cl.⁷ .................... G01N 33/26; G01N 19/02
(52) U.S. Cl. ......................................... 73/53.05; 73/10
(58) Field of Search .................... 73/53.05, 10, 152.18, 73/152.23, 152.22, 53.06, 61.41, 61.63

(56) References Cited

U.S. PATENT DOCUMENTS

| | | | | |
|---|---|---|---|---|
| 4,458,528 A | * | 7/1984 | Roper et al. | 73/152.49 |
| 4,548,080 A | * | 10/1985 | Sweet | 73/865.6 |
| 5,052,219 A | * | 10/1991 | Fery et al. | 73/152.22 |
| 5,167,143 A | * | 12/1992 | Brookfield | 73/54.23 |
| 5,616,842 A | * | 4/1997 | Armengaud et al. | 73/152.18 |
| 5,969,227 A | * | 10/1999 | Kenney | 73/10 |

FOREIGN PATENT DOCUMENTS

| | | | | |
|---|---|---|---|---|
| FR | 2758185 | * | 7/1998 | G01N/11/14 |
| GB | 2275342 | * | 8/1994 | G01N/11/14 |
| WO | 9830885 | * | 7/1998 | G01N/11/14 |

* cited by examiner

Primary Examiner—Hezron Williams
Assistant Examiner—Jay L. Politzer
(74) Attorney, Agent, or Firm—Thomas O. Mitchell; Catherine Menes; Brigitte Jeffery

(57) ABSTRACT

A method of determining the shear threshold of a drilling mud consists in placing a detecting head with a spherical surface near to a porous wall, in pouring the drilling mud around the detecting head, in forcing the mud to pass through the porous surface so as to form a mud cake above the porous surface and around the detecting head which has a diameter D, and in measuring both the time required for the mud cake to reach a measurable or pre-determined height, and also the torque opposing rotation of the detecting head corresponding to that height.

10 Claims, 2 Drawing Sheets

APPARATUS AND METHOD FOR MEASURING THE CHARACTERISTICS OF AN OILFIELD FLUID OR THE LIKE

The present invention relates to apparatus for measuring certain theological characteristics of an oilfield fluid or the like such as a drilling mud or a cement slurry. More particularly, the invention relates to evaluating the tendency of a drilling mud to stick and to the difficulty of eliminating the mud cake.

Drilling a well such as an oilfield, gas, geothermal, or analogous well necessitates the use of various fluids, the rheological characteristics of which must be known as precisely as possible, with measurements preferably being made at the drilling site while the fluid is being prepared. During the drilling operation proper, a fluid or drilling mud is circulated in the drilled hole, which mud acts, inter alia, to cool and lubricate the drilling tool, to lift drilling debris to the surface, to prevent ingress of formation fluid, in particular gas, and to maintain stability by preventing the walls from collapsing. Once the hole has been drilled, casing or coiled tubing is lowered into the hole and is cemented over all or a part of its height, with the cement slurry being injected via the inside of the tubing or casing to then fill the annular space between the tubing and the well wall. In addition to a mechanical function of maintaining the tubing or casing in position, the cementing isolates the various layers of formation traversed by the hole, prevents gas from rising via the annular space and limits the ingress of water into the production well. It also, of course, acts primarily to hold the casing in position.

Very schematically, a cement slurry is constituted by a liquid base (water and soluble additives), and solid materials (cement) in suspension in that base.

The drilling mud is principally constituted by a liquid base which is generally water, oil, or a water-in-oil emulsion type, by salts or other substances in solution in the base, and by solids which are insoluble in the base such as baryte or bentonite which are added to adjust the density and the viscosity of the fluid.

When a fluid is in contact with a relatively porous formation, and if the hydrostatic pressure of the formation is lower than the pressure of the drilling fluid, then the fluid will tend to penetrate into the formation. However, the pores of the formation are generally smaller in size than the solid particles suspended in the fluid. This leads to a filtration phenomenon with the liquid base and the finest solids flowing into the formation and with the less fine solid particles being deposited on the walls to form a cake, known as mud cake when the fluid is a drilling mud.

In itself, mud cake formation is a desirable phenomenon since it tends to render the well walls impermeable and thus limits drilling fluid loss. However, drillpipes, logging tools and casing elements can rub against and become stuck in the cake when such elements stop rotating for a prolonged period, which incidents are difficult to avoid since drilling mud is often circulated for periods which last for several months. Freeing an element stuck in the cake means that a very large torque has to be applied, which torque is not always immediately available and is also associated with a risk of breakage. As a result, drilling can be interrupted, leading to major overcosts.

United Kingdom patent GB-A-2 275 342 describes apparatus for evaluating the tendency of a drilling mud to stick by measuring the torque required to rotate a ball in contact with a porous surface through which a drilling mud is forced in order to form a cake. That apparatus can also measure the quantity of liquid which has flowed through the wall after 30 minutes (fluid loss measurement). However, the disadvantage of that apparatus is that it has been shown that the results are not always reproducible from one experimenter to another and in particular, the torque measured is systematically overvalued by a friction factor which depends on the type of drilling mud and which as a result is not a constant.

The apparatus known from GB-A-2 275 342 is constituted by a pressurised cell having a base which is formed by a grid with its surface facing the inside of the cell being covered with a filter paper in order to simulate the well wall. The cell is provided with a cover which is pierced at its centre by a passage for a rod having the ball fixed to its end. The cell is filled with the mud to be tested and the ball is lowered until it just touches the filter paper. A gas is injected above the mud to simulate the pressure difference between the mud and the formation fluids. As the height of the mud cake increases, the torque T required to initiate rotation of the ball is measured by a sensor associated with the rod. According to the model used by the authors, that torque is proportional to a sticking factor S which is characteristic of a given mud and to $t^{3/4}$, where t is the time over which the differential pressure is applied.

French patent application FR-A-2 758 185 describes an improvement to the apparatus described in the patent cited above, the improvement consisting in means, for example bearings, to keep a constant distance which is as small as possible but not zero between the ball and the filter paper, and in driving the ball using a magnetic transmission in order to be able to measure very small torques as are measured in particular with oil-based mud. The improved apparatus of the cited French application has the advantage of being easier to handle, more robust, and thus more suitable for use at a drilling site.

The physical principles on which the measurements of the sticking factor are based using the apparatus known from the two patents cited above are described in detail in IADC/SPE 35100 in an article by Reid, P. I., Meeten, G. H., Way, P. W., Clark, P., Chambers, B. D. and Gilmour entitled "Mechanisms Of Differential Sticking And A Simple Well Site Test For Monitoring And Optimizing Drilling Mud Properties". The value of the sticking factor is determined by assuming: that the height h of the cake increases in accordance with a function of the type $h=\beta t^{1/2}$, where $\beta$—or the growth factor—is constant for a given mud under fixed temperature and pressure conditions; that the growth of the mud cake is not affected by the ball; that there is no sliding at the cake/ball interface; and that the stress exerted by the mud cake is constant over the entire height of the cake (in other words, the cake is homogeneous over its entire height). On these assumptions, the torque T which must be exerted at a time t to cause the ball to rotate can be expressed using a function of the type $T=S (t^{1/2}-t_0^{1/2})^{3/2}$ where $t_0$ is the time between the start of measurements and the time when the mud cake reaches the lowest point of the ball, and S is a factor termed the sticking factor which is characteristic of a drilling mud at a given temperature and pressure.

The critical values for the sticking factor are determined experimentally, which means that new muds presenting high risk can be rejected.

Further, before carrying out the cementing operation, it is often desirable to clean off the mud cake. Depending on the mud used, this well wall cleaning operation will be easier or harder and in particular will depend on the shear rate of the mud. The shear rate forms part of the definition of the sticking factor, but until now, no procedure has been proposed for evaluating it.

The present invention aims to provide new procedures for determining the shear rate of a mud under given temperature and pressure conditions.

The invention provides a method of determining the shear threshold of a drilling mud, the method consisting in placing a detecting head with a spherical surface near to a porous wall, in pouring the drilling mud around the detecting head, in forcing the mud to pass through the porous surface so as to form a mud cake above the porous surface and around the detecting head which has a diameter D, and in measuring both the time required for the mud cake to reach a measurable or pre-determined height, and also the torque opposing rotation of the detecting head corresponding to that height.

In a first variation of the invention, the height of the mud cake is measured at the end of the test by measuring the impression left by the detecting head after forming the cake for a given time t.

In a second variation of the invention, the time required for the cake to reach the bottom of the detecting head is measured from at least two measurements made at two different distances between the porous wall and the detecting head.

In a third variation of the invention, the detecting head is provided with marks such that the torque measured varies substantially at the moment the mud cake reaches the height of one mark.

In all variations of the invention, the procedures proposed also enable the growth factor of the cake to be determined.

Further details and advantages of the invention become apparent from the description below made with reference to the accompanying drawings in which.

Figure 1:
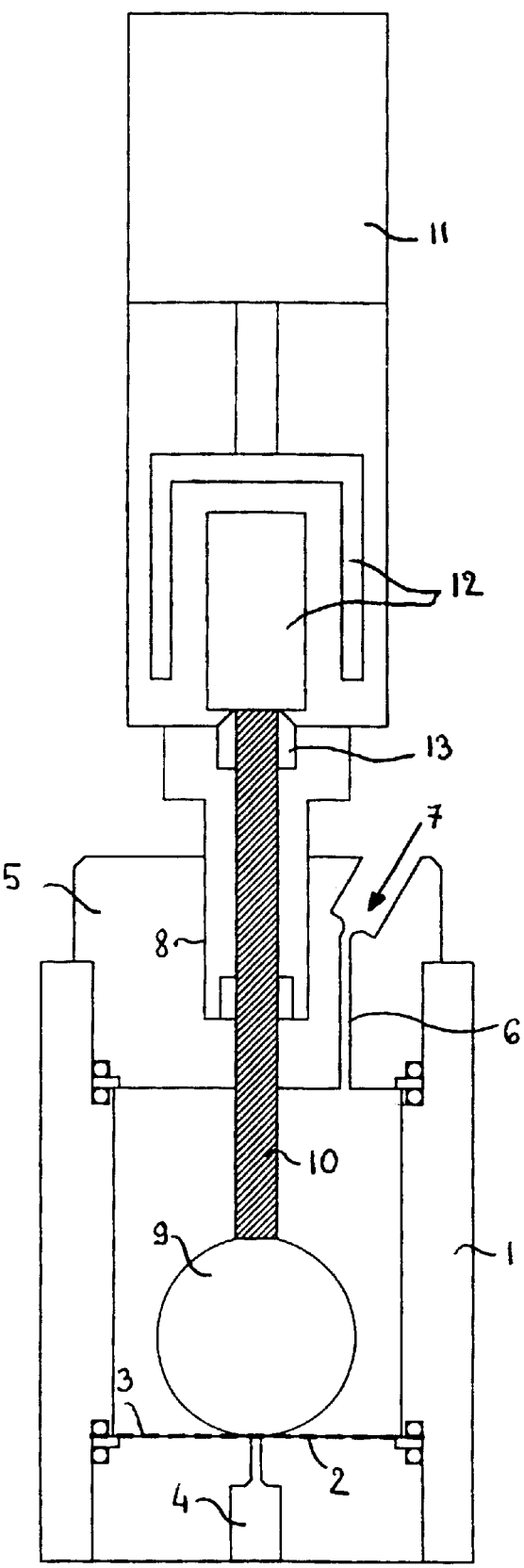
FIG. 1 is a diagrammatic view of apparatus of the invention for measuring the torque opposing rotation of the detecting head due to the formation of a mud cake.

Measuring apparatus as used for the two first procedures of the invention is shown in FIG. 1. It comprises a measuring cell which can be placed in a thermostatted bath. Cell 1 has a base 2 constituted by a grid, with its surface facing the inside of the cell being covered with a filter paper 3. A drain 4 beneath cell 1 enables the filtrate to be recovered.

The cell is closed by a cover 5 pierced by an opening 6 for a supply 7 of a nitrogen or carbon dioxide type gas used to pressurise the cell. Cover 5 is also provided at its centre with a passage 8 provided with a seal.

The detecting head is constituted by a ball 9 fixed to a shaft 10 driven in rotation by a drive system 11, via a magnetic transmission 12. Shaft 10 is supported by a bearing 13 comprising means for fine regulation of the vertical position of ball 9 so as to position the ball precisely so that it does not bear on grid 2 but remains suspended above it, at a small but non zero distance.

The value of the sticking factor is determined by assuming: that the height h of the mud cake increases in accordance with a function of the type $h=\beta t^{1/2}$, where $\beta$ is a constant for a given mud under fixed temperature and pressure conditions; that the growth of the mud cake is not affected by the ball; that there is no sliding at the cake/ball interface; and that the stress exerted by the mud cake is constant over the entire height of the cake (in other words the cake is homogeneous over its entire height). On these assumptions, it is possible to calculate that the torque T which must be exerted at a time t to rotate the ball can be expressed by a function of the type $T=S\,(t^{1/2}-t_0^{1/2})^{3/2}$ where $t_0$ is the time between the start of measurement and the instant when the mud cake reaches the lowest point of the ball, and S is factor which is characteristic for a drilling mud at a given temperature and pressure.

Using the method described in the above-cited SPE 35100 article, and further assuming that only the most compact portion of the mud contributes significantly to the torque exerted on the ball, the torque applied to the ball is the product of the shear rate $\tau_0$ of the mud and the surface area of the ball in contact with the mud. It can thus be shown that that torque can be expressed by the formula $$T = \frac{2\pi}{3} D^{3/2} \tau_0 h^{3/2},$$

where D is the ball diameter, $\tau_0$ is the shear rate of the mud and h is the height of the "compact" cake.

Replacing h with its time dependent function, a new equation is obtained:

$$T = S_f t^{3/4} \text{ where } S_f = \frac{2\pi}{3} D^{3/2} \tau_0 \beta^{3/2}$$

In a first procedure in accordance with the invention, consisting in two measurements, the height of the cake can be obtained by measuring the diameter d of the impression of the ball in the cake after a filtration test of duration t.

$$h = \frac{D}{2} - \sqrt{\frac{D^2}{4} - \frac{d^2}{4}}$$

From which it follows that:

$$\beta = \frac{\frac{D}{2} - \sqrt{\frac{D^2}{4} - \frac{d^2}{4}}}{t^{1/2}}$$

If the filtration test takes 30 minutes, or 1800 seconds, the shear rate $\tau_0$ can be determined from a single measurement of $d_{30}$ (diameter of the impression of the ball after 30 minutes) using the equation:

$$\tau_0 = \left[\frac{1800}{1 - \sqrt{1 - (d_{30}/D)^2}}\right]^{3/4} \frac{3 S_f}{2\pi D^3}$$

where diameters $d_{30}$ and D are expressed in meters and $S_f$ is expressed in Newtons per meter to the power ¾.

Clearly, the formula remains valid for the entire period of the test. Nevertheless, it is important that the period is sufficient for the cake to be properly formed. Also, accuracy is further improved when the test is carried out over a long period, but in general it is pointless to continue the test beyond one hour. More generally, the shear rate can be obtained using the formula:

$$\tau_0 = \left[\frac{t}{1 - \sqrt{1 - (d_t/D)^2}}\right]^{3/4} \frac{3 S_f}{2\pi D^3}$$

This first procedure is easy to carry out with muds that form a compact, well-defined cake, which is generally the case with water-based muds. With oil-based muds, the impression is present but it is generally masked by a layer of creamy consistency which must be removed with a spatula to reveal the impression.

For this reason, the authors of the present invention have developed a second procedure which more particularly requires an apparatus as described in French patent FR-A-2 758 185 which allows the distance between the ball and the porous wall (filter paper) to be adjusted finely.

In this second procedure, two tests are carried out one after the other, using a mud of the same composition and under the same temperature and pressure conditions, but varying the distance h between the filter paper and the ball. The test is stopped when the value of the torque starts to deviate significantly from the background noise. By assuming again that the growth factor of the mud is constant in value for a given mud, under the given measuring conditions, we have:

$$\beta = \frac{h_2 - h_1}{t_2^{1/2} - t_1^{1/2}}$$

and the shear rate can be derived from the following equation:

$$\tau_0 = \left[\frac{t_2^{1/2} - t_1^{1/2}}{h_2 - h_1}\right]^{3/2} \frac{3S_f}{2\pi D^{3/2}}$$

The height $h_1$ will typically be zero (the sphere is initially in contact with the filter) or any value in the range 0 to 0.1 millimeters (mm); the value of $h_2$ is selected so as to be close to 0.5 mm, for example.

This second procedure is more suitable for oil-based muds but it is not always easy to carry out two successive tests under conditions that are rigorously the same, especially if these tests have to be carried out at the drilling site.

For this reason, the authors of the present invention have developed a third procedure to determine the values of the growth factor $\beta$ and the shear rate $\tau_0$. This third procedure is derived from the second procedure and is also based on determining the time at the end of which the mud cake reaches a pre-defined height. For this reason, the ball is provided with marks or notches such that the torque is significantly modified when the mud cake reaches the height corresponding to these marks. The profile of the value of the torque exerted as a function of time thus includes points of inflexion which can be identified and which correspond to the moments when the cake height reaches the levels of the marks.

Figure 2:
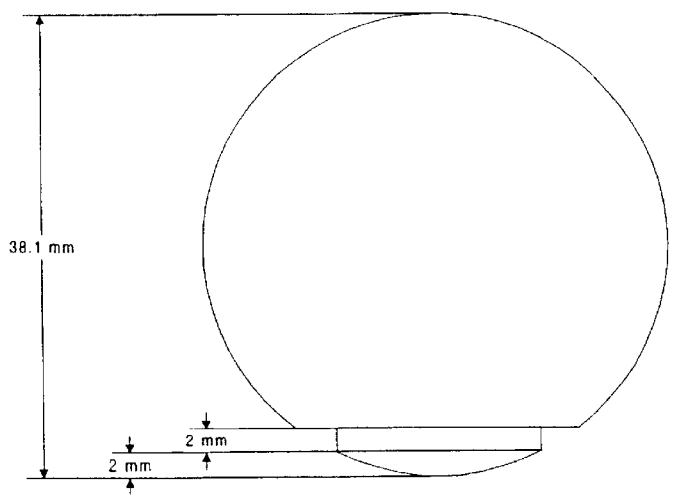
FIG. 2 is an example of a detecting head provided with marks used to carry out the third variation of the invention.

FIG. 2 shows an example of ball marks which have been machined to form a cylindrical portion of $h_2=2$ mm after a spherical portion with a height $h_1=2$ mm (of course, these heights can be different and need not be the same).

When the cake reaches the cylindrical portion under these conditions, the value of the torque becomes substantially smaller than the value of the torque for the lower portion of larger diameter. In contrast, the torque substantially increases at the end of the cylindrical portion.

Advantageously, the ball may contain a plurality of cylindrical portions, at different heights, such that whatever the growth factor of the mud cake, at least two marks will be reached in a period of less than 8 hours, for example. It should be noted that when the number of cylindrical portions (or any equivalent mark) is high, then it is no longer necessary to assume that the growth rate is constant (it suffices to assume that it is constant for the time interval between the two marks).

Since the value of $h_1$ is known accurately, and since the value of $t_1$ (or more exactly, $t_1^{3/4}$) is easily identifiable from the profile of the torque as a function $t^{3/4}$, the growth factor $\beta$ can be determined from the formula $$\beta = \frac{h_1}{t_1^{1/2}}$$

and the shear rate $\tau_0$ can be determined from the equation $$\tau_0 = \frac{h_1^{3/2}}{t_1^{1/2}} \frac{3S_f}{2\pi D^{3/2}}.$$

The same calculation can advantageously be repeated for $h_2$ and $t_2$ which means that errors due to poor positioning of the ball can be cancelled out. In this case, the value of the growth factor will preferably be obtained by applying the formula:

$$\beta = \frac{h_2 - h_1}{t_2^{1/2} - t_1^{1/2}}$$

the difference $h_2-h_1$ being fixed accurately by the geometry of the ball.

It should be noted that the accuracy of the measurement increases when the ratio between the height of the mud cake and the diameter of the ball is small. When the first spherical portion of the ball is over a small height (2 mm in the example in FIG. 2), it is possible to choose a large diameter without having to modify the proportions of the cell. In this case, the ball can clearly be replaced by a cap.

Figure 3:
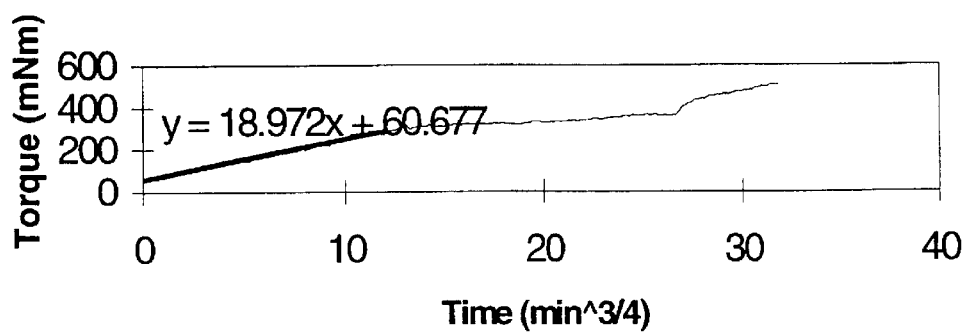
FIGS. 3 and 4 are profiles of the torque with time recorded using an apparatus as shown in FIG. 2.
Figure 4:
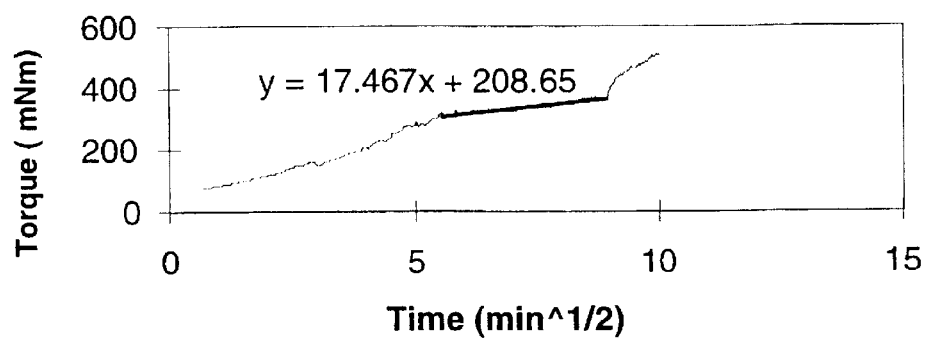

FIGS. 3 and 4 show curves representing the variation of the torque over time, for the two intervals $t_1$ and $t_2$, for the ball shown in FIG. 2, and for a mud comprising, in grams (g) in a volume of 5 liters (l):

| | |
|---|---|
| Water | 5208 g |
| Wyoming bentonite | 300 g |
| Chaillac barite | 2268 g |
| OCMA Clay | 210 g |
| CaCO3 (Meudon whiting) | 150 g |
| Quartz | 60 g | plus a few drops of a bactericide.

Times $t_1$ and $t_2$ can be respectively estimated as 28 minutes and 80 minutes. It has been shown that from 0 to $t_1$, the torque was proportional to $\tau_0\beta^{3/2}$ and that from $t_1$ to $t_2$ (corresponding to the cylindrical portion of the detecting head), the torque was proportional $2\pi r^2\beta\tau_0$, where r is the radius of the cylinder, from which a growth factor of 0.546 mm/min$^{1/2}$ is calculated. With a sticking factor of 18.9 mNm/min$^{3/4}$, the shear rate was 95 Pa.

What is claimed is:

1. A method of determining the shear threshold of a drilling mud, comprising the steps of placing a detecting head with a spherical surface near a porous wall in a measuring cell, pouring the drilling mud into the cell around the detecting head, forcing mud to pass through the porous surface to form a mud cake above the porous surface and around the detecting head and measuring both the time required for the mudcake to reach a measurable or predetermined height and the torque opposing rotation of the detecting head corresponding to said height, characterised in that during measurement, the inside of the cell is maintained at a predetermined pressure and temperature and the measured time is the time for a compact mudcake to reach the measurable or predetermined height and the torque is measured at this time, this time and torque being used to calculate the shear threshold of the drilling mud.

2. A method according to claim 1, characterized in that the growth factor of the mud is also determined.

3. A method according to claim 1, characterized in that the height of the mud cake is measured at the end of the test by measuring the impression left by the detecting head after forming the cake for a given period t.

4. A method according to claim 3, characterized in that the shear rate $\tau_0$ of the mud is also calculated, using the formula:

$$\tau_0 = \left[ \frac{t}{1 - \sqrt{1 - (d_t/D)^2}} \right]^{3/4} \frac{3S_f}{2\pi D^3}$$

where $S_f$ is the sticking factor of the tested mud, D is the diameter of the detecting head and $d_t$ is the diameter of the impression after time t.

5. A method according to claim 3, characterized in that the growth factor of the mud cake is calculated using the formula:

$$\beta = \frac{\frac{D}{2} - \sqrt{\frac{D^2}{4} - \frac{d_t^2}{4}}}{t^{1/2}}.$$

6. A method according to claim 1, characterized in that the time required for the cake to reach the bottom of the detecting head is measured from at least two measurements made at two different distances between the porous wall and the detecting head.

7. A method according to claim 6, characterized in that the times $t_1$ and $t_2$ required for the height of the cake to reach at least two pre-defined heights $h_1$ and $h_2$ are measured and the shear rate of the mud is calculated using the formula:

$$\tau_0 = \left[ \frac{t_2^{1/2} - t_1^{1/2}}{h_2 - h_1} \right]^{3/2} \frac{3S_f}{2\pi D^{3/2}}.$$

8. A method according to claim 1, characterized in that the detecting head is provided with marks such that the torque measured varies substantially at the moment the mud cake reaches the height of one mark.

9. A method according to claim 8, characterized in that said marks correspond to a cylindrical portion on the detecting head.

10. A method according to claim 9, characterized in that the shear rate of the mud is determined using the formula:

$$\tau_0 = \frac{h_1^{3/2}}{t_1^{1/2}} \frac{3S_f}{2\pi D^{3/2}}.$$

* * * * *